US011464474B2

(12) United States Patent
Akiyama et al.

(10) Patent No.: US 11,464,474 B2
(45) Date of Patent: Oct. 11, 2022

(54) MEDICAL IMAGE PROCESSING APPARATUS, X-RAY DIAGNOSTIC APPARATUS, AND MEDICAL IMAGE PROCESSING METHOD

(71) Applicant: TOSHIBA MEDICAL SYSTEMS CORPORATION, Otawara (JP)

(72) Inventors: Masaki Akiyama, Nasushiobara (JP); Yoshimasa Kobayashi, Nasushiobara (JP); Mika Takaya, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1055 days.

(21) Appl. No.: 15/837,023

(22) Filed: Dec. 11, 2017

(65) Prior Publication Data

US 2018/0160995 A1 Jun. 14, 2018

(30) Foreign Application Priority Data

Dec. 12, 2016 (JP) .............................. JP2016-240583
Dec. 7, 2017 (JP) .............................. JP2017-235265

(51) Int. Cl.
| | |
|---|---|
| *A61B 6/00* | (2006.01) |
| *A61B 6/12* | (2006.01) |
| *G06T 11/60* | (2006.01) |
| *G06T 7/00* | (2017.01) |
| *G06T 7/70* | (2017.01) |
| *G06T 19/00* | (2011.01) |

(52) U.S. Cl.
CPC .............. *A61B 6/5235* (2013.01); *A61B 6/12* (2013.01); *A61B 6/463* (2013.01); *A61B 6/485* (2013.01); *A61B 6/504* (2013.01); *G06T 7/0012* (2013.01); *G06T 7/70* (2017.01); *G06T 11/60* (2013.01); *G06T 19/00* (2013.01); *A61B 6/4441* (2013.01); *A61B 6/4464* (2013.01); *G06T 2207/10064* (2013.01); *G06T 2207/10121* (2013.01); *G06T 2207/30101* (2013.01); *G06T 2210/41* (2013.01)

(58) Field of Classification Search
CPC .................................................... A61B 6/5235
See application file for complete search history.

(56) References Cited

U.S. PATENT DOCUMENTS

2008/0183071 A1* 7/2008 Strommer ................. G06T 7/80
600/424
2013/0034283 A1 2/2013 Ohishi

FOREIGN PATENT DOCUMENTS

| JP | 2010-172350 | 8/2010 |
|---|---|---|
| JP | 2010-194046 | 9/2010 |
| JP | 2012-005636 | 1/2012 |
| JP | 2015-211914 | 11/2015 |

* cited by examiner

*Primary Examiner* — Joseph M Santos Rodriguez
(74) *Attorney, Agent, or Firm* — Oblon, McClelland, Maier & Neustadt, L.L.P.

(57) ABSTRACT

In one embodiment, a medical image processing apparatus used for a treatment using a device includes a memory configured to store a volume data of an object; and processing circuitry configured to acquire positional information of the device, set, in an X-ray image generated by imaging an object using X-ray, a region on which a volume-based 2D image generated from the volume data is to be superimposed, based on the positional information of the device, and generate a superimposed image by superimposing the volume-based 2D image on the set region in the X-ray image.

13 Claims, 8 Drawing Sheets

DISPLAY EXAMPLE 1 WHEN CATHETER KT REACHES FIXED REGION FR

DISPLAY EXAMPLE 2 WHEN CATHETER KT REACHES FIXED REGION FR

MEDICAL IMAGE PROCESSING APPARATUS, X-RAY DIAGNOSTIC APPARATUS, AND MEDICAL IMAGE PROCESSING METHOD

CROSS-REFERENCE TO RELATED APPLICATIONS

This application is based upon and claims the benefit of priority from Japanese Patent Application No. 2016-240583, filed on Dec. 12, 2016 and Japanese Patent Application No. 2017-235265 filed on Dec. 7, 2017, the entire contents of each of which are incorporated herein by reference.

FIELD

Embodiments described herein relate generally to a medical image processing apparatus, an X-ray diagnostic apparatus, and a medical image processing method.

BACKGROUND

In recent years, researches on angiography apparatuses for imaging blood vessels have been actively conducted. In X-ray fluoroscopy for imaging blood vessels, two-dimensional fluoroscopic images are acquired by enhancing a blood vessel with, e.g., a contrast medium. In a region where the running state of the blood vessel is complex, there are cases where it is difficult to grasp the running direction of a treatment device such as a catheter with only two-dimensional information.

Thus, a study has been made on a technique of generating a superimposed image by superimposing an image based on volume data of the object on a fluoroscopic image of the same object. This superimposed image is called a three-dimensional roadmap in some cases. Since it is possible to obtain three-dimensional information as well as two-dimensional information of a fluoroscopic image by referring to a three-dimensional roadmap, a doctor, who performs an interventional radiography (IVR), can more accurately grasp a running state of blood vessels.

However, when an image based on volume data is superimposed on a fluoroscopic image, this makes difficult to see a catheter itself and/or a branch portion of the blood vessels in the superimposed portion in some cases. As a result, the doctor cannot smoothly conduct treatment under IVR in some cases.

In addition, in some cases, an image based on volume data may be unnecessarily superimposed on a region where treatment of IVR is not needed, and thus the superimposed image based on the volume data may interfere with the doctor.

DETAILED DESCRIPTION

Hereinafter, embodiments of medical image processing apparatuses, X-ray diagnostic apparatuses, and medical image processing methods will be described with reference to the accompanying drawings.

In one embodiment, a medical image processing apparatus used for a treatment using a device includes a memory configured to store a volume data of an object; and processing circuitry configured to acquire positional information of the device, set, in an X-ray image generated by imaging an object using X-ray, a region on which a volume-based 2D image generated from the volume data is to be superimposed, based on the positional information of the device, and generate a superimposed image by superimposing the volume-based 2D image on the set region in the X-ray image.

First Embodiment

Figure 1:
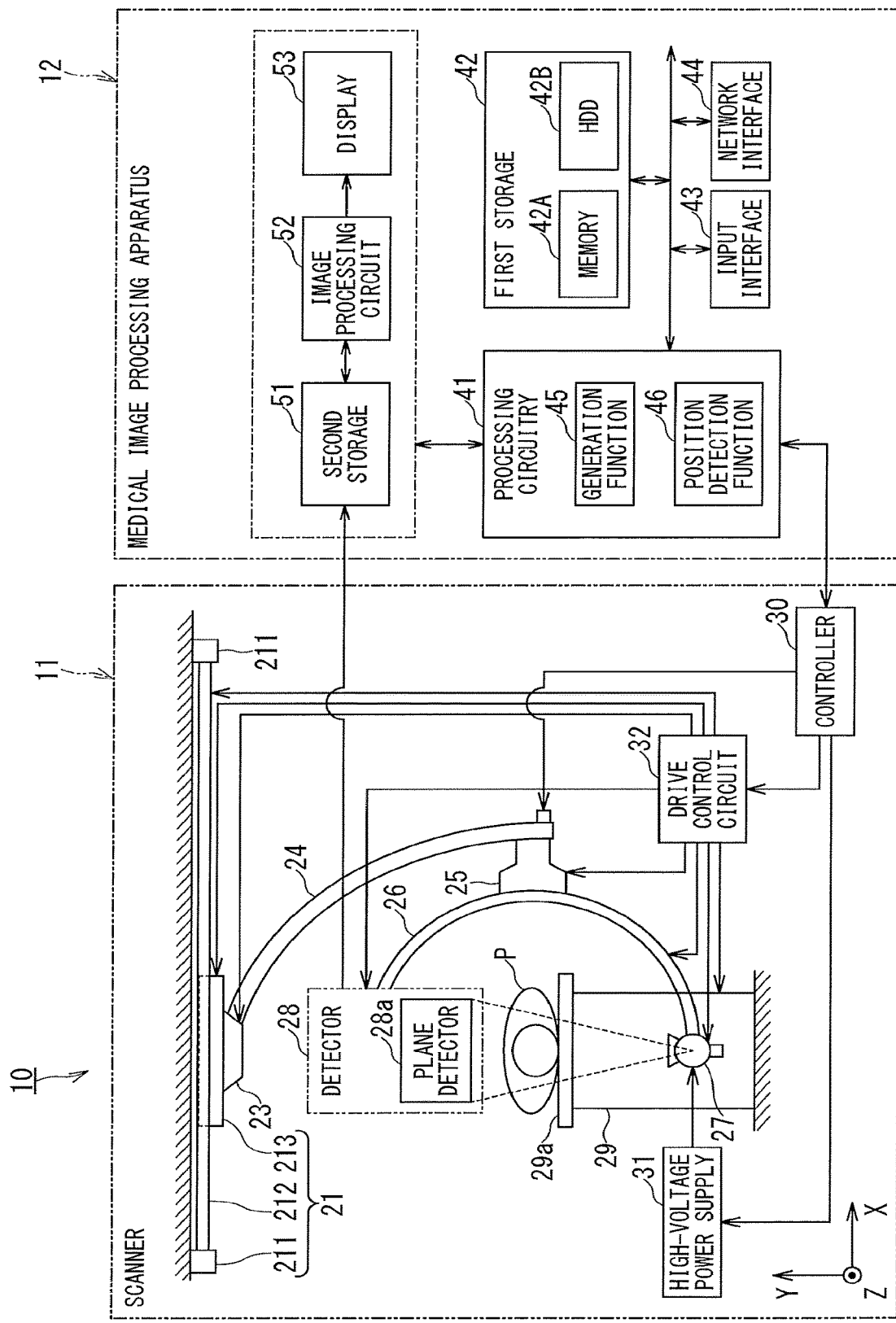
FIG. 1 is a block diagram illustrating respective configurations of a medical image processing apparatus and an X-ray diagnostic apparatus according to one embodiment.

FIG. 1 is a block diagram illustrating a configuration of an X-ray diagnostic apparatus 10 of the first embodiment that includes a medical image processing apparatus 12 of the first embodiment. As shown in FIG. 1, the X-ray diagnostic apparatus 10 includes a scanner 11 and the medical image processing apparatus 12. In general, the X-ray diagnostic apparatus 10 is installed in an examination room or a treatment room.

Figure 2:
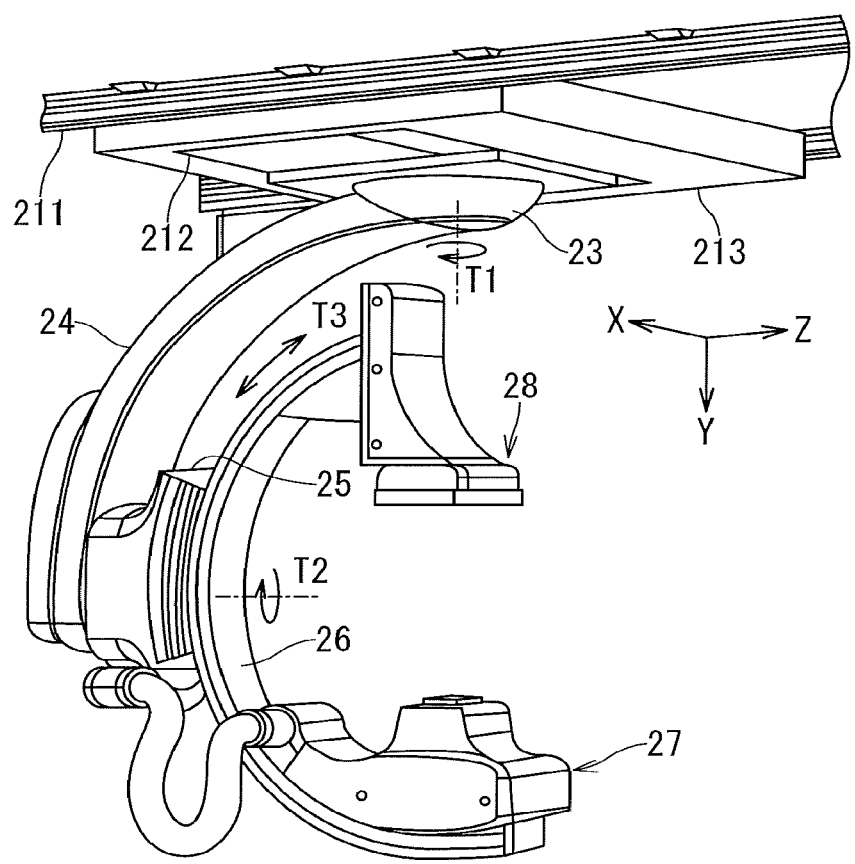
FIG. 2 is a perspective view illustrating an external configuration of a scanner of the X-ray diagnostic apparatus shown in FIG. 1.

FIG. 2 is a perspective view illustrating a configuration of the scanner 11. FIG. 1 and FIG. 2 illustrate a case where the X-ray diagnostic apparatus 10 is equipped with a ceiling suspended C-arm. However, the X-ray diagnostic apparatus 10 is not limited to a configuration equipped with a ceiling suspended C-arm hut may be equipped with a floor-traveling C-arm or a floor-mounted C-arm. Further, the X-ray diagnostic apparatus 10 may be configured such that its X-ray irradiator and its X-ray detector described below are separately supported by respective arms. Although a description will be given of a case where the X-ray diagnostic apparatus 10 is equipped with a C-arm, embodiments of the present invention are not limited to such an aspect.

Out of the scanner 11 and the medical image processing apparatus 12 included in the X-ray diagnostic apparatus 10, the scanner 11 will be described first in terms of configuration and operation. As shown in FIG. 1 and FIG. 2, the scanner 11 includes a slide mechanism 21, a vertical-axis rotation mechanism 23, a suspension arm 24, a C-arm rotation mechanism 25, a C-arm 26, an X-ray irradiator 27, an X-ray detector 28, a bed 29, a controller 30, a high voltage power supply 31, and a drive control circuit 32.

The slide mechanism 21 includes a Z-axis direction rail 211, an X-axis direction rail 212, and a carriage 213. The slide mechanism 21 integrally slides the vertical-axis rotation mechanism 23, the suspension arm 24, the C-arm rotation mechanism 25, the C-arm 26, the X-ray irradiator 27, and the X-ray detector 28 in the horizontal direction, under the control of the controller 30 via the drive control circuit 32.

The Z-axis direction rail 211 is installed so as to extend in the Z-axis direction (i.e., long-axis direction of the table 29a), and is supported by the ceiling.

The X-axis direction rail 212 is installed so as to extend in the X-axis direction (i.e., short-axis direction of the table 29a), and is supported on the Z-axis direction rail 211 via non-illustrated rollers at both ends thereof. The X-axis direction rail 212 is moved in the Z-axis direction on the Z-axis direction rail 211, under the control of the controller 30 via the drive control circuit 32.

The carriage 213 is supported on the X-axis direction rail 212 via non-illustrated rollers. The carriage 213 is moved in the X-axis direction on the X-axis direction rail 212 under the control of the controller 30 via the drive control circuit 32.

Since the X-axis direction rail 212 supporting the carriage 213 can move on the Z-axis direction rail 211 in the Z-axis direction, and the carriage 213 can also move on the X-axis direction rail 212 in the X-axis direction, the carriage 213 can move in the examination room horizontally (i.e., in the X-axis direction and the Z-axis direction).

The vertical-axis rotation mechanism 23 is rotatably supported by the carriage 213. The vertical-axis rotation mechanism 23 integrally rotates the suspension arm 24, the C-arm rotation mechanism 25, the C-arm 26, the X-ray irradiator 27, and the X-ray detector 28 in the vertical-axis rotation direction T1 (shown in FIG. 2) under the control of the controller 30 via the drive control circuit 32.

The suspension arm 24 is supported by the vertical-axis rotation mechanism 23.

The C-arm rotation mechanism 25 is rotatably supported by the suspension arm 24. The C-arm rotation mechanism 25 integrally rotates the C-arm 26, the X-ray irradiator 27, and the X-ray detector 28 in the rotation direction T2 with respect to the suspension arm 24 (shown in FIG. 2), under the control of the controller 30 via the drive control circuit 32.

The C-arm 26 is supported by the C-arm rotation mechanism 25, and disposes the X-ray irradiator 27 and the X-ray detector 28 such that the X-ray irradiator 27 and the X-ray detector 28 face each other with the object P interposed therebetween. A rail (not shown) is provided on the back surface or side surface of the C-arm 26. Via this rail interposed between the C-arm rotation mechanism 25 and the C-arm 26, the C-arm 26 causes the X-ray irradiator 27 and the X-ray detector 28 to integrally and circularly move in the circular arc direction (shown in FIG. 2) under the control of the controller 30 via the drive control circuit 32.

The X-ray irradiator 27 is provided at one end of the C-arm 26. The X-ray irradiator 27 is provided so as to be able to move forward and backward under the control of the controller 30 via the drive control circuit 32. The X-ray irradiator 27 includes an X-ray tube. The X-ray irradiator 27 receives high-voltage power from the high-voltage supply device 31 to radiate X-rays toward a predetermined part of the object P in accordance with the condition of high voltage power. The X-ray irradiator 27 is provided with components such as an X-ray irradiation-field diaphragm and a compensation filter on the emission side of X-rays. The X-ray irradiation-field diaphragm is composed of plural lead blades. The compensation filter is formed of, e.g., silicone rubber and attenuates a predetermined amount of irradiation X-rays in order to prevent halation.

The X-ray detector 28 is provided at the other end of the C-arm 26, i.e., on the opposite side of the emission of the X-ray irradiator 27. The X-ray detector 28 is provided so as to be able to move forward and backward under the control of the controller 30 via the drive control circuit 32. The X-ray detector 28 has a flat panel detector (FPD) 28a, detects X-rays by using detection elements arranged in a two-dimensional pattern, and converts the X-rays into a digital signal for each pixel.

The X-ray detector 28 may be, e.g., an image intensifier (I.I.)-TV system. In this case, the X-ray detector 28 may be configured to include an I.I.TV camera and an A/D (Analog to Digital) conversion circuit. As to the X-ray detector 28, it is sufficient that the X-ray detector 28 can detect X-rays that have passed through the object P or have been made incident thereon directly.

The bed 29 is supported on the floor surface and supports the table (i.e., catheter table) 29a. Under the control of the controller 30 via the drive control circuit 32, the bed 29 moves the table 29a horizontally (in the X-axis and Z-axis directions) or vertically (in the Y-axis direction) and rolls the table 29a. The table 29a is capable of placing the object P thereon and is movable. Although a description will be given of the scanner 11 of an undertube type in which the X-ray irradiator 27 is located under the table 29a, the scanner 11 may be configured as an overtube type in which the X-ray irradiator 27 is located above the table 29a.

The controller 30 includes a non-illustrated central processing unit (CPU) and a non-illustrated memory. The controller 30 controls operations of respective components such as the high voltage power supply 31 and the drive control circuit 32. The controller 30 can calculate the position of the bed 29 and the position of the table 29a by controlling respective components such as the drive control circuit 32 that drives the bed 29 and the table 29a.

The high voltage power supply 31 can supply high voltage power to the X-ray irradiator 27 under the control of the controller 30.

The drive control circuit 32 can drive each of the slide mechanism 21, the vertical-axis rotation mechanism 23, the C-arm rotation mechanism 25, the C-arm 26, the X-ray irradiator 27, the X-ray detector 28, and the table 29a of the bed 29 in accordance with control of the controller 30.

Next, a description will be given of the medical image processing apparatus 12 in terms of configuration and general operation. As shown on the right side of FIG. 1, the medical image processing apparatus 12 is configured of hardware components such as processing circuitry 41, a first storage 42, an input interface 43, a network interface 44, a second storage 51, an image processing circuit 52, and a display 53. The processing circuitry 41 is interconnected to the respective hardware components constituting the medical image processing apparatus 12 via a bus as a common signal transmission path. In addition, the processing circuitry 41 has a function of integrally or comprehensively controlling the medical image processing apparatus 12.

The processing circuit 41 includes a processor. The processor reads out and executes predetermined programs stored in the memory 42A of the first storage so as to implement various functions defined by the programs.

The above-described term "processor" means, e.g., a circuit and/or a device such as a special-purpose or general-purpose CPU (central processing unit), an ASIC (application specific integrated circuit), an FPGA (field programmable gate array), and a programmable logic device including a SPLD (simple programmable logic device) and a CPLD (complex programmable logic device).

The processor implements the respective functions by reading out programs stored in a memory or programs directly stored in the circuit thereof and executing the programs. When the processing circuitry 41 is provided with plural processors, the memory 42A for storing the programs may be provided for each of the processors or the memory 42A of the first storage 42 in FIG. 1 may store all the programs corresponding to the functions of the respective processors.

The first storage 42 includes, as the memory 42A, components such as a ROM (Read Only Memory) and a RAM (Random Access Memory). The memory 42A may store data of IPL (Initial Program Loading) and BIOS (Basic Input/Output System) in addition to the above-described various programs. Further, the memory 42A may be used as a work memory of the processing circuit 41 or may be used for temporary storage of data.

The first storage 42 further includes, e.g., an HDD (Hard Disk Drive) 42B. The HDD 42B stores data and programs (including an operating system in addition to application programs) installed in the medical image processing apparatus 12. Further, it is possible to make the operating system (OS) to provide a GUI (Graphical User Interface) in which graphics are frequently used for displaying information to a doctor and by which basic manipulations can be performed via the input interface 43.

Either the memory 42A or the HDD 42B of the first storage 42 stores volume data of the object P to be described below.

The input interface 43 is a circuit for inputting a signal from an input device such as a keyboard and a pointing device (e.g., a mouse) that can be operated by an operator such as a doctor (i.e., a medical doctor who is in charge of the IVR) and/or a medical-examination technician. In the present embodiment, the input device is assumed to be included in the input interface 43. In the present embodiment, an input signal in accordance with an operation is transmitted from the input interface 43 to the processing circuitry 41.

The network interface 44 performs communication control according to each communication standard. The network interface 44 has a function of being connected to a non-illustrated network through, e.g., a telephone line and/or a dedicated line.

The second storage 51 stores detection data outputted from the A/D conversion circuit of the X-ray detector 28 of the scanner 11 under the control of the processing circuitry 41. In addition, the second storage 51 stores fluoroscopic images and radiographic images outputted from the image processing circuit 52 under the control of the processing circuitry 41. The second storage 51 stores fluoroscopic images before image processing and radiographic images before image processing (i.e., so-called original images). The medical image processing apparatus 12 is configured to cause the image processing circuit 52 to perform necessary image processing to display the fluoroscopic images and/or radiographic images after image processing on the display 53.

Under the control of the processing circuitry 41, the image processing circuit 52 generates fluoroscopic images and radiographic images from the detection data stored in the second storage 51. Although a fluoroscopic image and a radiographic image are both X-ray images, a fluoroscopic image is an image which is imaged with a relatively low X-ray dose. A fluoroscopic image is an image for observing the state of a blood vessel and/or the state of a device such as a catheter inserted into the blood vessel on a real-time basis, so that the fluoroscopic image is time-sequentially generated for the same position of the same patient to constitute a moving image having a predetermined frame rate. The action or operation for acquiring a time-sequential fluoroscopic image is referred to as "fluoroscopic imaging" in some cases. Further, the operation mode for acquiring a time-sequential fluoroscopic image is referred to as "fluoroscopy mode" in some cases.

On the other hands, the radiographic image is an image which is imaged with an X-ray dose higher than that of a fluoroscopic image. Although a radiographic image is usually a still image, a time-sequential radiographic image can also be a moving image. Since a radiographic image is imaged with a higher X-ray dose than a fluoroscopic image, the quality of the radiographic image is higher than a fluoroscopic image. The action or operation of acquiring a radiographic image is referred to as "radiographic imaging" in some cases. In addition, the operation mode for acquiring a radiographic image is referred to as "radiographic mode" in some cases.

For instance, when a doctor performs IVR while referring to fluoroscopic images, the medical doctor may desire to record a specific state in this operation. In such case, the doctor may temporarily shift the X-ray diagnostic apparatus from the fluoroscopic mode to the radiographic mode to obtain the radiographic image with high quality, and then shift back the X-ray diagnostic apparatus to the fluoroscopic mode again to continue IVR in some cases.

The image processing circuit 52 generates a fluoroscopic image and a radiographic image on the basis of the detection data acquired in the fluoroscopy mode and radiographic mode, respectively. The generated fluoroscopic image and radiographic image are temporarily stored in the second storage 51.

The image processing circuit 52 further performs predetermined image processing on the fluoroscopic image and the radiographic image stored in the second storage 51. The predetermined image processing includes, e.g., enlargement/gradation/spatial-filter processing on data, minimum-value/maximum-value tracing processing of time-sequentially accumulated data, and addition processing for removing noise. The data subjected to the image processing by the image processing circuit 52 are outputted to the generation function 45 and the position detection function 46 of the processing circuitry 41.

Next, a description will be given of the generation function 45 and the position detection function 46 implemented by the processing circuitry 41. The processor of the processing circuitry 41 implements the generation function 45 and the position detection function 46 by reading out and executing predetermined programs.

The generation function 45 generates a superimposed image by superimposing a "volume-based 2D image" on the above-described fluoroscopic image acquired in real time during IVR. Meanwhile, the position detection function 46 detects the position of a device such as a catheter, which is used for implementing the IVR, in real time. Further, the generation function 45 performs processing for setting or changing a superimposed region of the "volume-based 2D image" and the fluoroscopic image in the superimposed image on the basis of the information on the detected position of the device. A more detailed description of each of these functions will be given below. The display 53 displays the superimposed image generated by the generating function 45. The display 53 may display only the fluoroscopic image or only the radiographic image.

Here, a "volume-based 2D image" to be superimposed on the fluoroscopic image will be described. "Volume data" means three-dimensional image data which are previously generated by imaging the same object as the target of fluoroscopic images (i.e., target of IVR) prior to the IVR. The volume data can be generated by reconstructing plural projection images which have been acquired by imaging the same object while the C-arm 26 of the X-ray diagnostic apparatus 10 of the present embodiment is being rotated. Alternatively, the three-dimensional image data of the same object acquired by a modality different from the X-ray diagnostic apparatus 10, e.g., an X-ray CT apparatus or an MRI apparatus can be used for the above-described "volume data".

The "volume-based 2D image" is an image generated by processing of projecting the above-described volume data on a two-dimensional plane. That is, the "volume-based 2D image" is an image generated by applying a rendering processing on the volume data. A method of rendering processing is not limited to a specific one, and various types of rendering processing such as a ray casting method or an MIP (Maximum intensity Projection) method can be adopted. It is assumed that the projection direction used for the rendering processing is made to substantially match the imaging direction of the fluoroscopic images.

In the following description, the "volume-based 2D image", i.e., an image generated by performing the rendering processing on volume data is referred to as a "rendering image".

For instance, a rendering image may be generated by the processing circuitry 41 using the volume data of the object P read out from the first storage 42, or may be generated by the image processing circuit 52. The generated rendering images are stored in, e.g., the first storage 42.

Next, a description will be given of processing of the medical image processing apparatus 12 of the first embodiment with reference to the flowchart shown in FIG. 3.

First, in the step S001, when a doctor manipulates the input interface 43 to press the start button of the three-dimensional roadmap, the medical image processing apparatus 12 starts fluoroscopic imaging of the object P and starts generation of a time-sequential fluoroscopic image. For instance, the image processing circuit 52 generates a fluoroscopic image on the basis of the detection data outputted from the X-ray detector 28 of the scanner 11.

In the next step S003, the medical image processing apparatus 12 reads out volume date from the first storage 42 when the doctor manipulates the input interface 43, for instance. As described above, the volume data is, e.g., three-dimensional image data that have been generated by reconstructing plural projection images generated in advance by the X-ray diagnostic apparatus 10 and/or three-dimensional image data of the same object that have been generated by an X-ray CT apparatus or an MRI apparatus.

In the next step S005, the medical image processing apparatus 12 generates a rendering image from the volume data and further generates a superimposed image by superimposing the rendering image on the fluoroscopic image generated in real time. In this case, the processing circuitry 41 of the medical image processing apparatus 12 generates the rendering image such that the projection direction (i.e., rendering direction) of the volume data matches the imaging direction of the fluoroscopic image. In advance of generation of each superimposed image, the alignment processing is performed between the fluoroscopic image and the rendering image as the preprocessing.

In the next step S007, as the doctor manipulates the input interface 43, the medical image processing apparatus 12 receives a setting of the display method for the superimposed image. For instance, the medical image processing apparatus 12 according to the first embodiment receives such a setting of the display method for the superimposed image that a rendering image within a region including a device, which is used in IVR such as a catheter, is not depicted in the superposed image, on the basis of the position of the device. In the following description, it is assumed that the device is a catheter.

In the next step S009, the processing circuitry 41 displays the superimposed image while modifying it in accordance with the selected setting of the display method for the superimposed image. For instance, the processing circuitry 41 causes the display 53 to display the superimposed image such that a superimposed region is changed based on the position of the catheter (or in association with movement of the catheter) and such that a region including the catheter in the rendering image is not depicted, based on the position of the catheter. In other words, processing circuitry 41 causes the display 53 to display the superimposed image such that a region including the catheter in the rendering image is not superimposed on the fluoroscopic image, based on the position of the catheter. In addition, the processing circuitry 41 moves a non-depicted region where the rendering image is not depicted in the superimposed image, depending on the movement of the catheter during IVR.

Figure 4A:
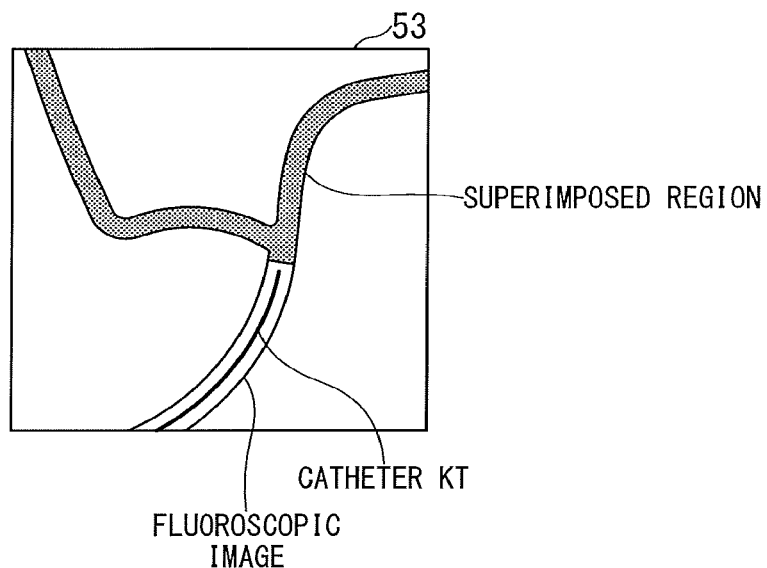
FIG. 4A and FIG. 4B are schematic diagrams illustrating a case where a range of a region in a rendering image to be superimposed is changed and a non-display region in the rendering image is moved in accordance with movement of a catheter.
Figure 4B:
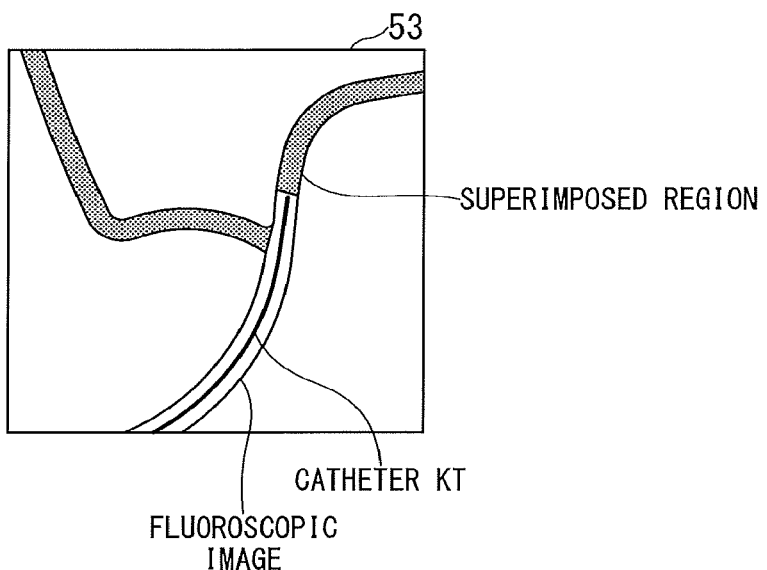

FIG. 4A and FIG. 4B illustrate blood vessel images displayed on the display 53. Each of these blood vessel images is a superimposed image in which a fluoroscopic image and a rendering image are superimposed. In each superimposed image of the first embodiment, at least one superimposed region is changed in association with movement of the catheter KT, such that a region including the catheter KT of the rendering image is not depicted in the superimposed image.

Among the superimposed images shown in FIG. 4A and FIG. 4B, gray hatched areas indicate superimposed regions, in each of which a fluoroscopic image and a rendering image are superimposed. Each of the white regions indicates a region in which only the fluoroscopic image is displayed without superimposing a rendering image (i.e., the rendering image is not depicted). Note that the gray and white regions in FIG. 5A to FIG. 7B also indicate the same correspondence relationship as that in FIG. 4A and FIG. 4B.

Note that, in in the first embodiment, in the superimposed image, in which a fluoroscopic image and a rendering image are superimposed, a region including the catheter K in the rendering image is not depicted. Further, it should be noted that the region including the catheter KT is not limited to a region including one position of the catheter KT such as its tip but may be a region including plural positions in the catheter KT. The region including the catheter KT may be a region of a predetermined length of the insertion tool extending from the tip of the catheter KT toward its insertion position.

For instance, the processing circuitry 41 of the medical image processing apparatus 12 detects the position of the catheter KT from the fluoroscopic image by the position detection function 46 in the case of FIG. 4A, and then, the processing circuitry 41 display the superimposed image such that a region including the catheter KT in the rendering image is not depicted, based on the position of the catheter KT.

Meanwhile, FIG. 4B illustrates a case in which the position of the catheter KT, which is moving, is detected from the fluoroscopic image by the position detection function 46 of the processing circuitry 41 and the superimposed region in the display 53 is changed in accordance with the movement of the catheter KT. In other words, the processing circuitry 41 displays the superimposed image such that a region where the rendering image is not depicted is moved, depending on a movement of the catheter KT. Specifically, FIG. 4B shows a display example in which the superimposed region of the rendering image and the fluoroscopic image moves as the catheter KT moves upward in FIG. 4B.

Returning to FIG. 3, in the step S011, imaging is performed to acquire a radiographic image as needed. In normal fluoroscopic imaging, a fluoroscopic image is time-sequentially imaged as a real-time moving image. However, there are cases in which it is desired to examine the object with a high quality radiographic image imaged by setting high X-ray dose, and there are cases where it is desired to store such high quality radiographic image. In such cases, by operating the input interface 43, the doctor can acquire radiographic images by increasing X-ray dose more than X-ray dose during fluoroscopic imaging.

In the step S013, it is determined whether fluoroscopic imaging is completed or not. The medical image processing apparatus 12 waits for an instruction as to whether fluoroscopic imaging is to be ended or not. When the display method of the superimposed image is changed and fluoroscopic imaging is continued, the processing returns to the step S007 as shown in FIG. 3. When fluoroscopic imaging is continued without changing the display method of the superimposed image, the processing returns from the step S013 to the step S009.

As described above, the medical image processing apparatus 12 according to the first embodiment can generate a superimposed image by superimposing a volume-based 2D image of the object P (i.e., rendering image) on a fluoroscopic image acquired by performing fluoroscopic imaging on the object P, and further change the superimposed region of the rendering image in the superimposed image on the basis of the position of the catheter moving during IVR.

Thus, when the doctor moves the catheter, the rendering image superimposed on the fluoroscopic image neither hides a necessary region in the fluoroscopic image nor interferes with the doctor. As the result, the doctor can smoothly perform the operation (i.e., the IVR) using the catheter.

According to the display method of the first embodiment shown in FIG. 4A and FIG. 4B, in the superposed image in which the fluoroscopic image and the rendering image are superimposed, only the fluoroscopic image is depicted and the rendering image is not superimposed on the region including the catheter KT. However, the first embodiment is not limited to such a display method.

First Modification of First Embodiment

The medical image processing apparatus 12 according to the first modification of the first embodiment causes the display 53 to display the superimposed image, such that not only a region including the catheter KT but also an additional region in the rendering image, located a predetermined distance or more away from the tip of the catheter KT in a traveling direction of the catheter KT, is not depicted.

In other words, in the display method according to the first modification of the first embodiment, the fluoroscopic image and the rendering image are superimposed, and the superimposed region is displayed only in a limited region a predetermined distance away from the tip position of the catheter KT, while other than the superimposed region, only the fluoroscopic image is displayed. This type of display method also can be set in the step S007 of FIG. 3.

Figure 5A:
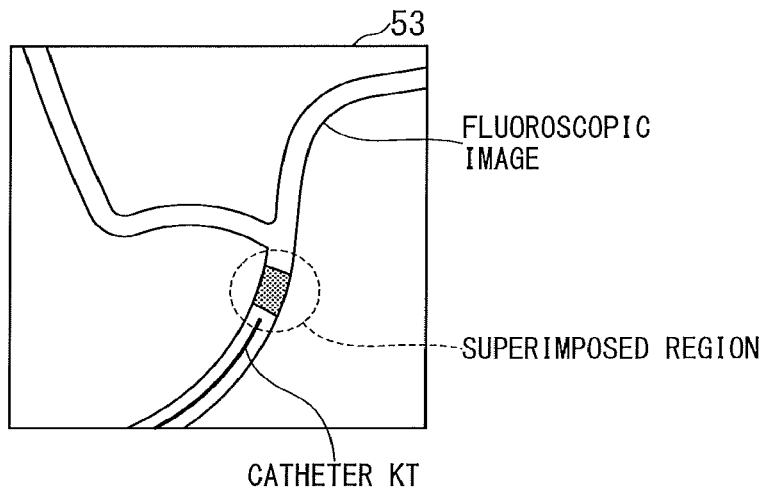
FIG. 5A and FIG. 5B are schematic diagrams illustrating a display setting in which the region of the rendering image to be superimposed and displayed is in the vicinity of the tip of the catheter and outside of the path of the catheter.
Figure 5B:
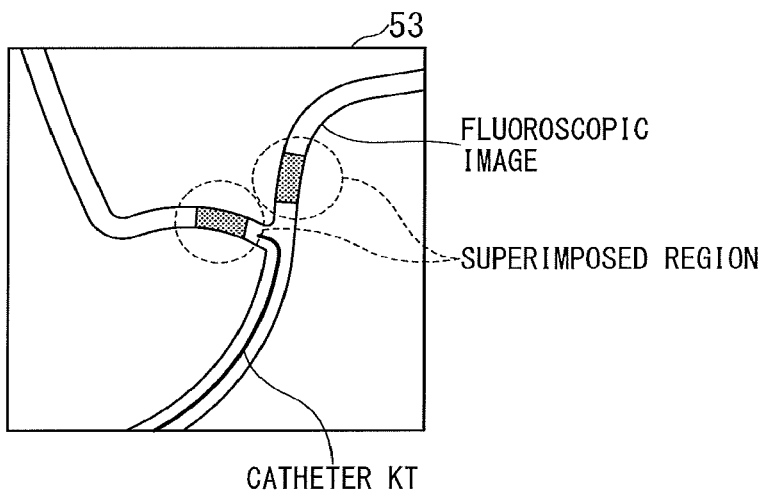

FIG. 5A and FIG. 5B are schematic diagrams illustrating the display method of the first modification of the first embodiment.

As shown in FIG. 5A and FIG. 5B, in each superimposed image displayed on the display 53, only the region in a predetermined range ahead of the tip position of the catheter KT is set to be the superimposed region, in which the fluoroscopic image and the rendering image are superimposed. In FIG. 5A, the rendering image is superimposed only in the region slightly ahead of the tip of the catheter KT, and in all the regions other than the superimposed region, the rendering image is not displayed as a non-depicted region where the rendering image is unnecessary. For instance, the range of superimposing the rendering image can be set to a range starting from the position 1 mm ahead of the tip of the catheter KT to the position 5 mm ahead of the tip. In this case, even for regions away from the tip of the catheter KT by 5 mm or more, the rendering image is not depicted, i.e., is not superimposed on the fluoroscopic image.

FIG. 5B illustrates a situation in which the superimposed region moves as the catheter KT moves. For instance, when there is a branch point of a blood vessel, it is possible to clearly indicate the existence of the branch at the tip of the catheter KT, and thus the doctor can easily identify the branch of the blood vessels in the fluoroscopic image.

Second Modification of First Embodiment

In the display method according to the first modification described above, the medical image processing apparatus 12 is configured to display, on the display 53, a superimposed image in which the rendering image is superimposed only in the vicinity of the tip of the catheter KT. By contrast, in the display method according to the second modification of the first embodiment, a positionally fixed superimposed region is constantly and additionally displayed regardless of the position of the catheter KT.

Figure 6A:
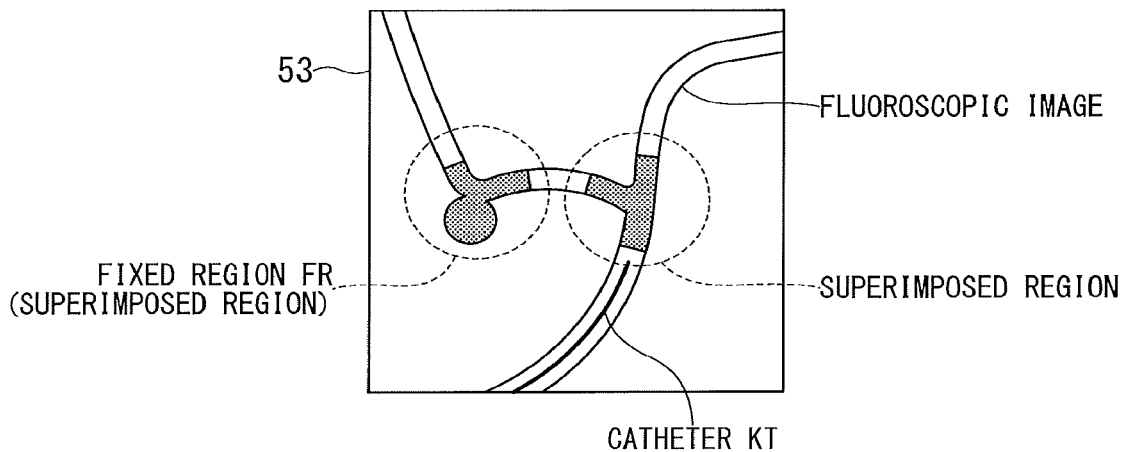
FIG. 6A to FIG. 6C are schematic diagrams illustrating a case in which a fixed region for fixedly displaying the rendering image is further set in the superimposed display shown in FIG. 5A and FIG. 5B.
Figure 6B:
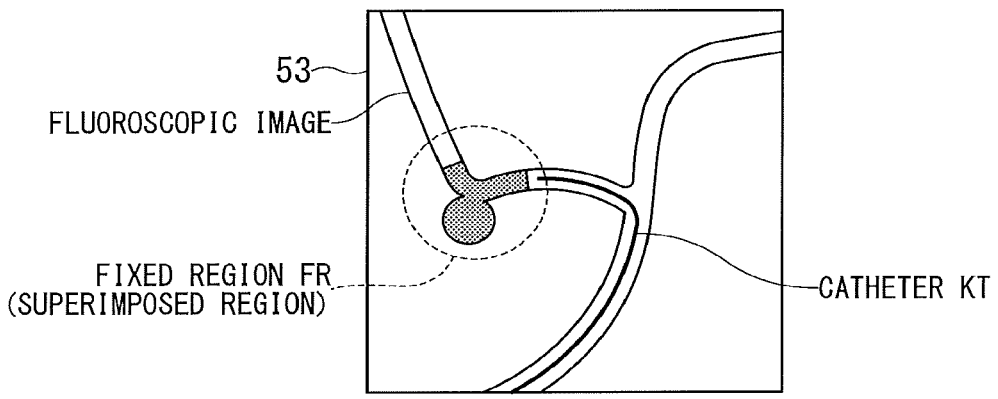
Figure 6C:
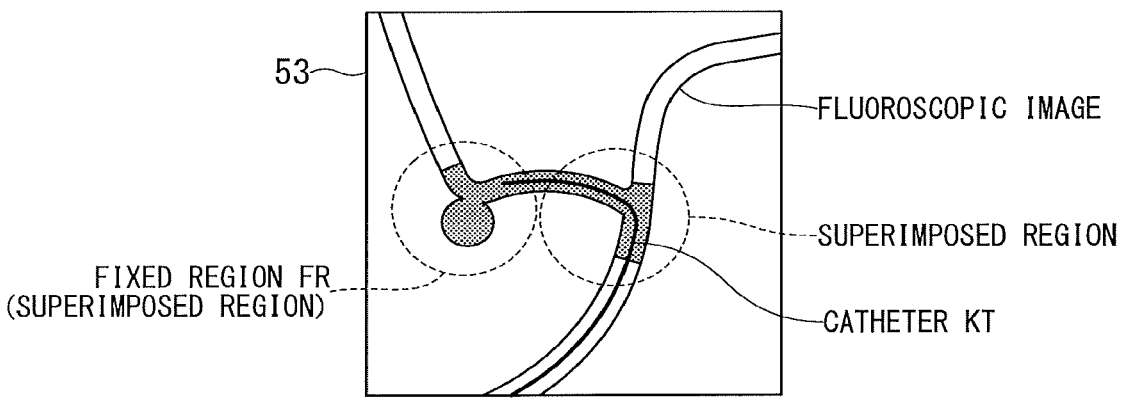

FIG. 6A to FIG. 6C are schematic diagrams illustrating the display method according to the second modification of the first embodiment.

FIG. 6A to FIG. 6C illustrate a display in which a fixed area FR for fixedly displaying the rendering image is further provided in the superimposed image to be displayed on the display 53. The rendering image for the fixed region FR displayed in FIG. 6A does not move even when the rendering image positioned near the tip of the catheter KT moves depending on the movement of the catheter KT.

Since an aneurysm and/or a varix in a blood vessel is a part to be examined at all times, a region corresponding to an aneurysm or varix is set, for example. as a fixed region FR.

FIG. 6B is a schematic diagram (display case 1) illustrating a state in which the tip of the catheter KT has reached to the fixed region FR in accordance with the movement of the catheter KT. In this state, the rendering image positioned near the tip of the catheter KT as shown in FIG. 6A has been disappeared, and only the fixed region FR is depicted as the superimposed region.

The method of displaying the fixed region FR is not limited to the above-described cases. For instance, the medical image processing apparatus 12 may treat the rendering image in the fixed region FR as the non-display region in association with the movement of the catheter KT, or may always display the rendering image in the superimposed region. Additionally, the display method of the catheter KT may be changed when the catheter KT has reached the fixed region FR.

FIG. 6C is a schematic diagram (display case 2) illustrating a case where the catheter KT has reached the fixed region FR. In FIG. 6C, for example, the rendering image is superimposed on the fluoroscopic imaging around the branch of the blood vessel so that the branch of the blood vessel can be clearly recognized. The above-described display methods are merely examples, and the rendering image may be superimposed on all the regions of the blood vessel, through which the catheter KT has passed, at a timing when the catheter KT has reached to the fixed region FR.

Usually, a frame rate of 30 frames per second is used to a standard real-time fluoroscopic imaging. However, a rate for generating the superimposed image is not necessarily the same frame rate as the fluoroscopic imaging. For instance, even when the frame rate for the real-time fluoroscopic imaging is 30 frames per second, the frame rate for the superimposed image may be 15 frames per second.

Second Embodiment

According to the first embodiment, the processing circuitry 41 of the medical image processing apparatus 12 does not display the rendering image at the region including the catheter KT in the superimposed image based on the position of the catheter KT (i.e., the rendering image is treated as the non-display region at the region including the catheter KT in the rendering image).

By contrast, according to the display method of the second embodiment, the processing circuitry 41 of the medical image processing apparatus 12 changes the superimposed image such that the rendering image even in a region including catheter KT is depicted. For instance, the rendering image and the fluoroscopic image are superimposed in both the region including the catheter KT and the region in the predetermined range ahead of the tip position of the catheter KT, while in all the other regions, the rendering image is not displayed.

Figure 7A:
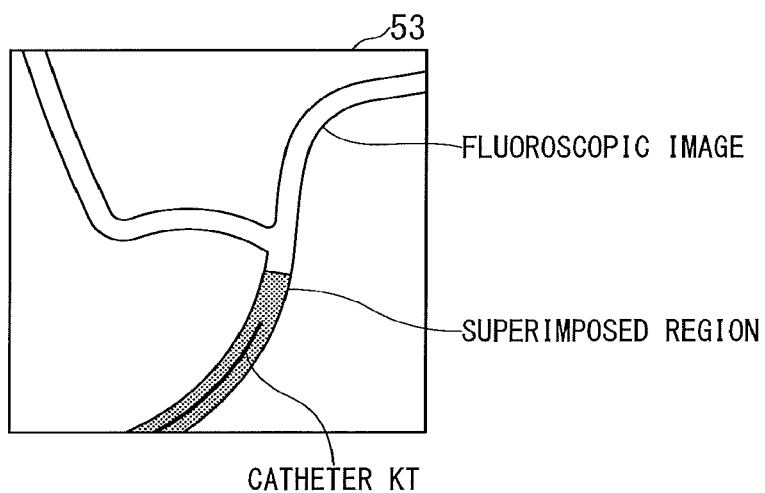
FIG. 7A and FIG. 7B are schematic diagrams illustrating a display setting in which a rendering image is superimposed and displayed including a catheter in conjunction with movement of a catheter during fluoroscopic imaging.
Figure 7B:
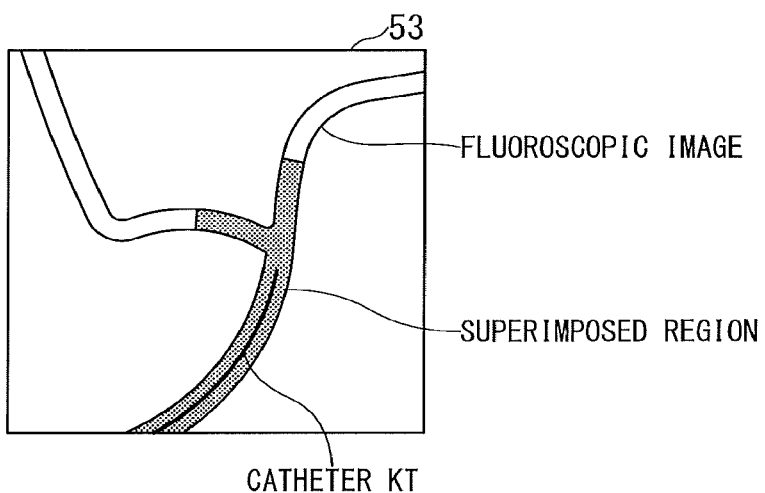

FIG. 7A and FIG. 7B are schematic diagrams illustrating the display method of the second embodiment.

As shown in FIG. 7A, in the display method according to the second embodiment, the region including the catheter KT is further added as the superimposed region to the superimposed region of the display method of the first modification of the first embodiment (FIG. 5A and FIG. 5B).

FIG. 7B illustrates a situation where the superimposed region moves as the catheter KT moves.

There may be some doctors who desire to observe the region including the catheter KT in the state where the rendering image is superimposed on the fluoroscopic image. In order to respond to the needs of such doctors, it is preferable that not only the display method of the first embodiment but also the display method of the second embodiment can be selected.

Further, in the first and second embodiments, the processing circuitry 41 may transparently superimpose the rendering image on the fluoroscopic image in the superimposed image on the basis of the position of the catheter KT.

For instance, in a branch point or a blocked part of a blood vessel, superimposition of a rendering image may cause difficulty in viewing. For this reason, the rendering image positioned at a branch point or blocked part of a blood vessel may be superimposed with higher transparency than that of a normal rendering image. The setting for the transparency can be set in the step S007 of FIG. 3.

Further, a superimposed image may be generated such that the transparency of the rendering image is set based on the position of the device, and then the rendering image having the set transparency is superimposed on the fluoroscopic image. In this case, in each of the above-described embodiments, the region, in which the rendering image is not depicted, corresponds to a region in which the rendering image having large transparency is superimposed on the fluoroscopic image (i.e., a region where the component of the rendering image is set to be smaller than the component of the fluoroscopic age).

Although a description has been given of cases where the position of a device such as a catheter is detected from at least one fluoroscopic image so far, the method of detecting the position of the device is not limited thereto. For instance, a sensor for detecting the position of the device may be separately provided so that the position of the device such as the catheter is detected by using the output of this sensor.

Figure 3:
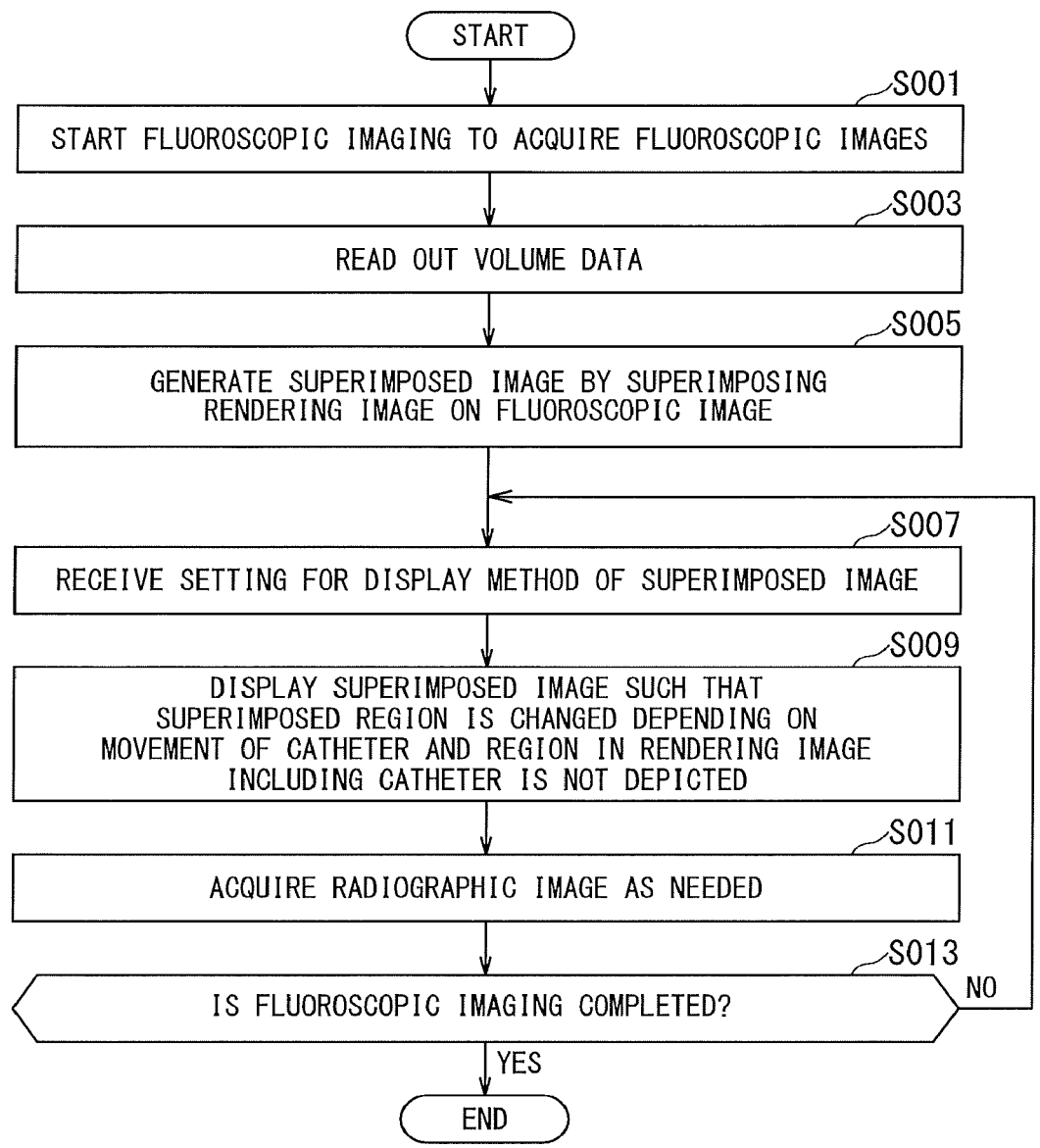
FIG. 3 is a flowchart illustrating superimposed-region change processing in which the medical image processing apparatus displays a superimposed image where a rendering image is superimposed on a fluoroscopic image such that a superimposed region can be changed.
Figure 8:
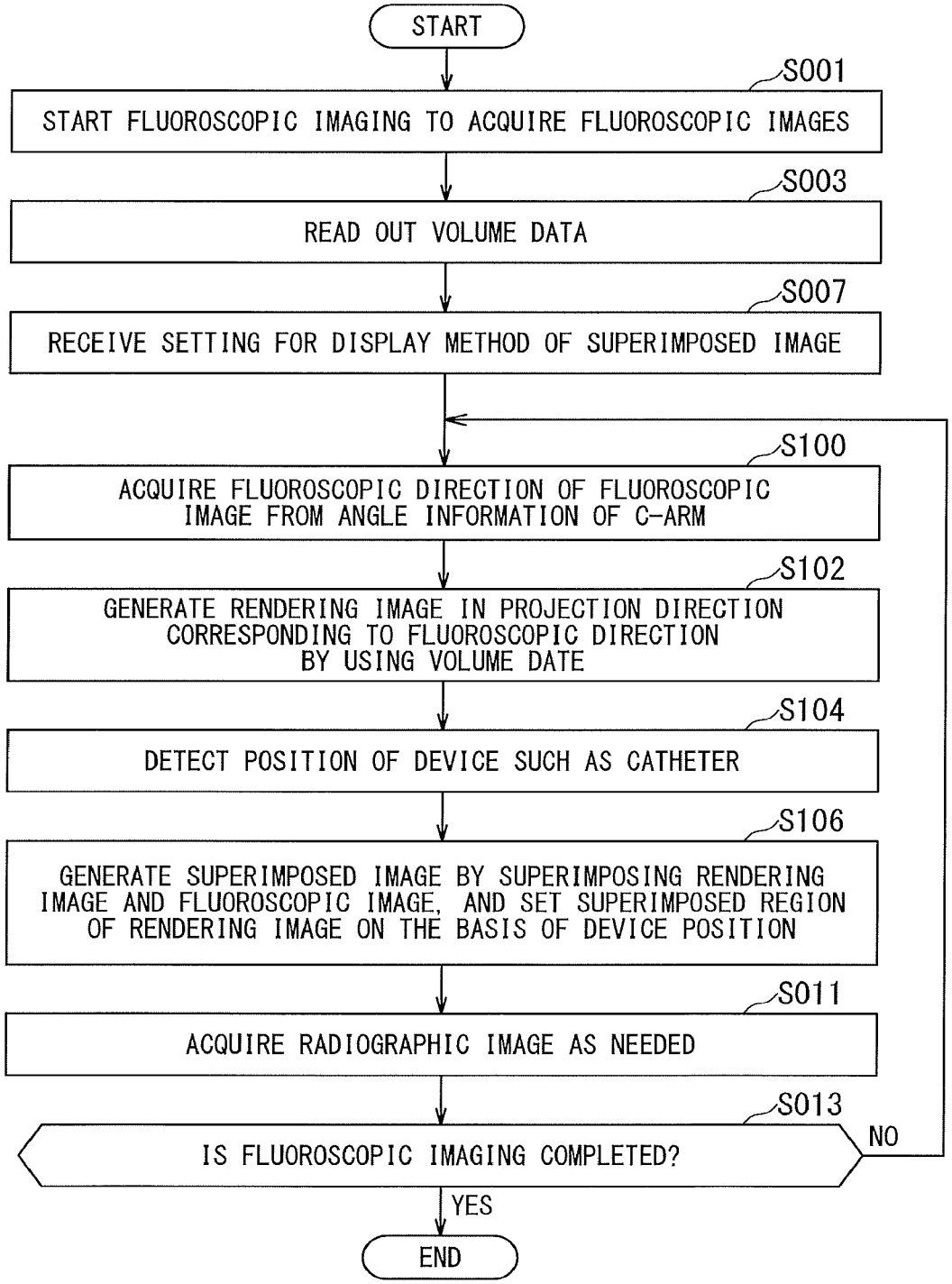
FIG. 8 is a flowchart illustrating a modification of the superimposed-region change processing.

Finally, FIG. 8 shows a flowchart corresponding to a modification of the superimposed-region change processing shown in FIG. 3. The same reference sign is assigned to the same processing as the processing in FIG. 3, and duplicate description is omitted.

In the processing shown in FIG. 8, after the step S003 subsequent to the step S001, the processing of the step S007 is performed to receive a setting of the fluoroscopic image display method.

In the next step S100, the X-ray fluoroscopic direction (i.e., imaging direction) of the fluoroscopic image is acquired from the angle information of the C-arm 26.

In the next step S102, a rendering image, which is rendered from the projection direction corresponding to the X-ray fluoroscopic direction, is generated from the volume data.

In the next step S104, the position of a device such as a catheter is detected from, e.g., one or plural fluoroscopic images.

In the next step S106, the superimposed region of the rendering image is set in the fluoroscopic image, on the basis of the detected device position, and the superimposed image is generated by superimposing the rendering image on the set superimposed region in the fluoroscopic image.

Alternatively or in addition, in the step S106, a transparency with which the rendering image is to be superimposed may be set in the fluoroscopic image, on the basis of the detected device position, and the superimposed image may be generated by superimposing the rendering image with the set transparency on the fluoroscopic image.

The processing of the step S106 corresponds to the steps S005 and S009 in FIG. 3. The superimposed image generated in the step S106 is displayed on the display 53. The processing in the steps S011 and S013 is the same as in FIG. 3.

According to at least one of the embodiments described above, when the doctor moves the catheter, the rendering image superimposed on the fluoroscopic image never interferes with the operation by the doctor, and thus, the doctor can smoothly conduct the operation.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical image processing apparatus used for a treatment using a device, the apparatus comprising:
    a memory configured to store a volume data of an object; and
    processing circuitry configured to
        acquire a real-time X-ray image by imaging an object using X-ray,
        acquire positional information of the device,
        generate a superimposed image by superimposing a volume-based 2D image generated from the volume data on the real-time X-ray image such that a superimposed region where the volume-based 2D image is superimposed and a non-depicted region where the volume-based 2D image is not superimposed are set based on the positional information of the device, and
        move a position of the superimposed region and a position of the non-depicted region, in accordance with a movement of the device.

2. The medical image processing apparatus according to claim 1,
    wherein the positional information of the device includes coordinates of a tip portion of the device.

3. The medical image processing apparatus according to claim 2,
    wherein the positional information of the device further includes coordinates of a portion of the device other than the tip portion of the device.

4. The medical image processing apparatus according to claim 1,
    wherein the processing circuitry is configured to display the superimposed image such that a region including the device in the volume-based 2D image is not depicted based on the positional information of the device.

5. The medical image processing apparatus according to claim 4,
    wherein the processing circuitry is configured to display the superimposed image such that the region where the volume-based 2D image is not depicted is moved depending on a movement of the device.

6. The medical image processing apparatus according to claim 5,
    wherein the processing circuitry is configured to display the superimposed image such that an additional region in the volume-based 2D image, located a predetermined distance or more away from a tip of the device in a traveling direction of the device, is not further depicted.

7. The medical image processing apparatus according to claim 6,
    wherein the processing circuitry is configured to
        receive setting of a fixed region where the volume-based 2D image is fixedly displayed, and
        display the superimposed image such that the fixed region in the volume-based 2D image is fixedly depicted regardless of the movement of the device, while the region including the device and the additional region in the volume-based 2D image are moved, depending on the movement of the device.

8. The medical image processing apparatus according to claim 1,
    wherein the X-ray image is a real-time X-ray image.

9. The medical image processing apparatus according to claim 1,
    wherein the processing circuitry is configured to
        set a transparency at each position of the volume-based 2D image in the superimposed image, based on the positional information of a device,
        superimpose the volume-based 2D image, which has the set transparency, on the X-ray image.

10. A medical image processing apparatus used for a treatment using a device, the apparatus comprising:
    a memory configured to store a volume data of an object; and
    processing circuitry configured to
        acquire a real-time X-ray image by imaging an object using X-ray,
        acquire positional information of the device,
        generate a superimposed image by superimposing a volume-based 2D image generated from the volume data on the real-time X-ray image such that a superimposed region where the volume-based 2D image is superimposed and a transparent region where the volume-based 2D image is superimposed with a predetermined transparency are set based on the positional information of the device, and
        move a position of the superimposed region and a position of the transparent region, in accordance with a movement of the device.

11. An X-ray diagnostic apparatus that comprises the medical image processing apparatus of claim 1.

12. An X-ray diagnostic apparatus that comprises the medical image processing apparatus of claim 10.

13. A medical image processing method comprising:
    acquiring a real-time X-ray image by imaging an object using X-ray,
    acquiring positional information of a device; and
    at least one of:
        (a) generating a superimposed image by superimposing a volume-based 2D image on the real-time X-ray image such that a superimposed region where the volume-based 2D image is superimposed and a non-depicted region where the volume-based 2D image is not superimposed are set based on the positional information of the device, and
        moving a position of the superimposed region and a position of the non-depicted region, in accordance with a movement of the device, and
        (b) generating a superimposed image by superimposing a volume-based 2D image generated from the volume data on the real-time X-ray image such that a superimposed region where the volume-based 2D image is superimposed and a transparent region where the volume-based 2D image is superimposed with a predetermined transparency are set based on the positional information of the device, and
        moving a position of the superimposed region and a position of the transparent region, in accordance with a movement of the device.

* * * * *